United States Patent [19]

Woodford

[11] Patent Number: 4,843,020

[45] Date of Patent: Jun. 27, 1989

[54] METHOD FOR DETECTING TETRAHYDROCANNABINOL IN HUMAN URINE INVOLVING MELANIN PRECIPITATION

[76] Inventor: W. James Woodford, 585 Lakeshore Dr., NE., Atlanta, Ga. 30307

[21] Appl. No.: 143,973

[22] Filed: Jan. 14, 1988

[51] Int. Cl.⁴ .................... G01N 33/534; G01N 33/94
[52] U.S. Cl. .................................... 436/518; 436/161; 436/173; 436/175; 436/177; 436/536; 436/804; 436/816; 436/825; 436/901
[58] Field of Search ............... 436/175, 816, 825, 901, 436/161, 173, 177, 536, 804

[56] References Cited

U.S. PATENT DOCUMENTS 4,022,878  5/1977  Gross .............................. 436/816 X
4,353,886  10/1982  Lukens ........................... 436/805 X Primary Examiner—Sidney Marantz
Attorney, Agent, or Firm—Jones, Askew & Lunsford

[57] ABSTRACT

An improved method for the detection of tetrahydrocannabinol in human urine wherein the pigment melanin is precipitated out of the urine prior to analysis with a solution of nitroferricyanide so that the melanin does not interfere with the analysis. The value attributable to melanin can also be subtracted from the value obtained during the analysis of the urine. The precipitation of melanin prior to analysis or subtraction of the melanin value during analysis greatly reduces the occurrence of false positive test results for persons with dark skin.

16 Claims, 1 Drawing Sheet

METHOD FOR DETECTING TETRAHYDROCANNABINOL IN HUMAN URINE INVOLVING MELANIN PRECIPITATION

TECHNICAL FIELD

The present invention relates to an improved method for detecting tetrahydrocannabinol in human urine, and more specifically relates to a sample preparation procedure in which the pigment melanin is removed from urine samples before analysis or subtracted from the value obtained during analysis to ensure the elimination of racial prejudice in test results.

BACKGROUND ART

Urinalysis testing for the detection of tetrahydrocannabinol (THC) or its metabolites has become prevalent in the workplace. THC is an active ingredient in the illegal drug marijuana. The U.S. Armed Forces routinely screens personnel for illegal drug use, often discharging those who test positive. Many companies now screen job applicants for evidence of illegal drug use and will refuse employment to applicants with positive results. Some employers conduct random urinalysis test of their employees to identify potential drug abusers. Employees having even minimum detectable levels of a THC metabolite in their urine are frequently dismissed.

The drug testing procedures used by testing laboratories often detect very small levels of the metabolites of THC in the urine; however, there has been evidence that these test results yield an abundance of false positives. In other words, many innocent people can be dismissed or refused employment because their urine indicates small amounts of a substance which was erroneously identified as a THC metabolite.

Survey results from the Council on Marijuana and Health and the National Institute on Drug Abuse show that white and non-white people have maintained approximately equivalent marijuana-use prevalence rates. In 1971, 150 out of every 1000 persons, whether white or non-white, was reported to have used marijuana within one month prior to the survey. By 1982, the prevalence rates for white users was 4% higher than the rate for non-whites. However, when urine samples are analyzed for the presence of THC metabolites, an unexplainably higher number of non-whites test positive.

As an example of these skewed results, a group of police cadets in Cleveland, Ohio, were tested for marijuana use one month before their graduation from the police academy. Ten out of 20 Black and Hispanic cadets tested positive for marijuana use; whereas, a THC metabolite was detected in the urine samples of only three out of 20 White cadets. All of the cadets knew they were to be tested and maintained that they had not used marijuana.

These results indicate that there may be an abnormally high number of false positives associated with non-white test subjects. The present invention has indicated that the pigment melanin can be responsible for the false positive test results for marijuana use. It is undisputed that there is more melanin in the urine of dark-skinned people than in light-skinned people. Schwartze, G., Bohlke, R., Effects of Different Skin Diseases, Skin Color and Season on Indolemelanogen Content in Urine, *Dermatol, Monatsschr.* Vol. 161[8], pp. 617-621, 1975. Furthermore, the size and structure of melanin and THC metabolite fragments are similar. Consequently, marijuana testing procedures are unable to properly differentiate between melanin and marijuana.

There has been evidence that melanin molecules accumulate or "self-assemble" in body fluids after the fluids have been removed from the body. Changes in pH and temperature appear to cause this accumulation. Therefore, the amount of melanin detected in a urine or blood sample will increase with time, making the occurrence of false positives more likely with samples that have been stored for a longer duration. Due to the fact that there is a larger initial concentration of melanin in persons with darker skin, it is even more likely that elevated levels of accumulated melanin in stored samples from dark-skinned individuals will give rise to a greater number of false positive test results.

A solution of sodium nitroferricyanide, otherwise known as the Thormahlin reagent, has been used by clinicians to detect urinary melanin for medical diagnostic purposes, such as for detection of melanoma. Melanin is detected by observance of a color change after the addition of sodium nitroferricyanide to an aliquot of urine. If melanin is present in the sample, the mixture will change from a normal straw color to green, blue, brown or black. A green coloration indicates that low levels of melanin are present in the sample. Blue indicates the presence of slightly more melanin, and brown or black indicates such high levels of melanin that melanoma might be suspected.

Two methods of drug testing for THC metabolites are commonly used: immunoassay and gas chromatography/mass spectrometry (GC/MS). The immunoassay method provides a postiive test result when a receptor, or antibody, supposedly combines with a fragment of a THC metabolite molecule contained in the urine sample. Normally, the immunoassay test kit contains a solution of radioactively labeled receptors which are specific for a THC metabolite. When the receptor solution is combined with a urine sample containing the THC metabolite, the THC metabolite will attach to the receptor generating a positive signal. If no THC metabolites are present, no binding will occur and the result should be negative.

Endogenous substances and normal body chemicals having a molecular structure similar to THC metabolites, can be mistakenly recognized by assay receptors and GC/MS detectors as false indicators of marijuana use. For example, *Comments on the Decision of the Comptroller General* (regarding Solicitation No. DLA120-84-R-0774, 1985) about marijuana immunoassay testing, attributed a poor (48%) test confirmation rate (page 8) to "non-users whose body chemistry may mimic low level use (i.e., actually false positives)". In addition, the National Institute on Drug Abuse has observed that some endogenous compounds have been noted to have the same GC/MS test characteristics as controlled substances, *Research Monograph*, 32, pp. 22-23. Melanin is but one such body chemical that can mimic THC metabolites in the urinalysis testing of non-users.

The GC/MS method for determining the presence of THC metabolites in urine involves the use of an analytical instrument known as a gas chromatograph coupled with a mass spectrometer. The gas chromatograph separates many of the components present in urine. One by one, each component is introduced into the mass spectrometer where it is bombarded with electrons causing fragmentation into ions. If the component is a THC metabolite, it will be broken down into many ions including ions having mass to charge ratios (m/z) of 372, 357 and 313. Often a known amount of an internal standard such as a deuterated THC metabolite is added to each urine sample for purposes of quantitation. The deuterated metabolite is fragmented into ions having m/z of 375, 360 and 316. A GC/MS spectrum of all the ions in the sample can be compared to a standard spectrum for the THC metabolite and its deuterated metabolite to determine whether the sample contains the THC metabolite.

There are differences of opinion among researchers as to how many ion-points of comparison, found in the GC/MS spectrum, are needed to confirm the presence of marijuana metabolites. A full-scan GC/MS spectrum (a 100% spectrum comparison) contains 23 major ion-points and numerous minor ion-points for comparison in the urinalysis testing process. A spokesman for Hewlett-Packard, a leading U.S. manufacturer of the widely used GC/MS testing equipment, reportedly recommended that for detecting a controlled substance, 83% of the major ion-points, comprising a partial GC/MS spectrum, are needed (see *Analytical Chemistry*, Volume 51, No. 8, p.818-A, 1979). For marijuana testing, 19 of the 23 major ion-points in the THC metabolite GC/MS spectrum would meet manufacturer's 83% spectrum match specifications. In contrast, a professor from the University of California, testifying in a military court martial, expressed the opinion that 9 ion-points of comparison (39% match) should be used for marijuana testing. *U.S. v. Lasley*, SPS, 244-98-1754. Still another opinion by the United States chief of drug testing research technology recommends "at least four points of comparison" (*Substance Abuse Report*, Volume 17, No. 4,p.7, 1986). Four points would constitute only a 17% spectrum comparison leaving reasonable doubt about the accuracy of the test result.

Various drug testing laboratories, offering economical urinalyses for employment and court related purposes, routinely rely on fewer than four ion-points in their GC/MS confirmation tests for marijuana. Numerous court cases are already on record wherein the drug testing laboratory gained a conviction based on detecting merely one point (4% match) in the marijuana GC/MS fingerprint comparison step.

Laboratories generating four or more points generally proceed with a computer assisted ratio-match step; however, the computers generally allow a wide plus-or-minus variance in the matching process. A laboratory employing merely three points and allowing a maximum variance in the ratio match step cannot possibly guarantee that the substance is marijuana.

The GC/MS technique is very sensitive and can detect very small levels of a THC metabolite in the urine, even as low as 1 to 5 ng/ml. A false positive test result can therefore occur with the GC/MS technique if another urine component fragments into the same ions as the THC metabolite molecule. Due to the extreme sensitivity of the GC/MS technique, it is possible that low levels of a naturally occurring substance, such as melanin, might give rise to false positive test results for marijuana. Persons having darker skin would therefore be more susceptible to receiving false positive test results because they have higher levels of melanin in their urine.

Therefore, there is a need for a urine test that does not yield racially biased results due to structural similarities between THC and melanin.

SUMMARY OF THE INVENTION

In accordance with the present invention, an improved method for determining THC or its metabolites in human urine samples is provided. The improved method eliminates the abnormally high number of false positive results for non-white individuals due to the presence of the pigment melanin.

In the first preferred embodiment, the improved method first precipitates a quantity of the pigment melanin from the urine specimen by combining the urine specimen with a de-melanizing agent, so that the urine specimen is substantially de-melanized. The de-melanized urine specimen is then analyzed according to conventional analytical techniques. Preferably, the de-melanizing agent is a solution of nitroferricyanide.

The de-melanized urine specimen may be analyzed by either an immunoassay technique, such as a radioimmunoassay, or by GC/MS, wherein selective ion monitoring may be utilized.

In the second embodiment, the analytical instrument, such as GC/MS, is adjusted to subtract an appropriate amount of the signal generated by the melanin.

Accordingly, it is an object of the present invention to provide an improved method for the detection of THC metabolites in human urine samples.

Another object of the present invention is to provide a method for the detection of THC that is not racially biased.

Another object of the present invention is to provide a method for the detection of THC that does not give a disproportionate number of false positive results for urine samples obtained from non-white individuals.

Another object of the present invention is to provide a method for the detection of THC that does not yield false positives due to the structural similarities between melanin and THC.

These and other objects, features and advantages of the present invention will become apparent after a review of the following detailed description of the disclosed embodiment and the appended claims.

DETAILED DESCRIPTION

Figure 1:
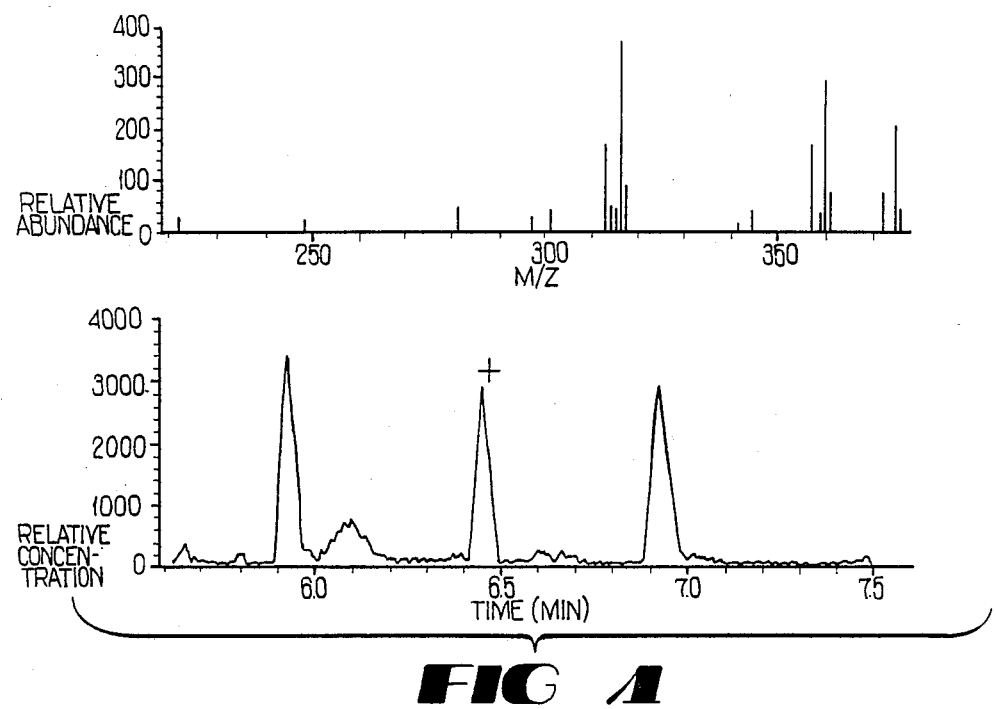
FIG. 1 is a representative chromatogram and bar charts or mass spectrum, showing the relative abundance of each ion fragment present in the peak identified as a THC metabolite prior to sample demelanization in accordance with the present invention.

The preferred embodiment of the present invention comprises an improved method for detecting a THC metabolite in human urine samples in which the melanin naturally present in a human urine specimen is removed prior to urinalysis.

Removal of melanin in a human urine sample in accordance with the process of the present invention is accomplished by treating said human urine samples with a sufficient amount of a demelanizing agent to react with and precipitate any melanin which may be present in said sample. Demelanizing agents in accordance with the present invention include solutions of sodium nitroferricyanide, acidified ferric chloride in water, hydroquinone (p-dihydroxybenzene), monobenzone (monobenzyl ether of hydroquinone), an ammoniacal silver nitrate solution in water, or certain mono-and dihydroxybenzene derivates such as catachol; 4-t-butylcatechol; 3-methylcatechol; 3,4-dihydroxyphenylalanine; 3,4-dihydroxyphenylacetic acid; and 4-methoxyphenol. The preferred demelanizing agent of the present invention is a solution of sodium nitroferricyanide (Thormalhlin reagent). Sodium nitroferricyanide is preferred because it reacts with the N-functional groups present in melanin but not present in the THC metabolite. The preparation of the foregoing demelanizing agents, which are all well known melanin detecting agents, is within the ability of those skilled in the art.

Sodium nitroferricyanide is used in the preferred embodiment of the present invention to react with melanin which may be present in a urine sample prior to analysis by immunoassay or GC/MS analysis. Several drops of a solution of sodium nitroferricyanide, having a concentration of approximately 25-75mg/ml, are added to an aliquot of urine contained within a test tube or other conventional sample container. Preferably, the aliquot will be between 1 and 10 ml urine. The pH of the urine-nitroferricyanide solution is adjusted so that it is weakly alkaline, and the solution is mixed for a short amount of time, preferably between 30 seconds and 5 minutes. The solution is then cooled to a temperature between approximately 15° C. and 25° C., preferably by immersion of the test tube in a bath of cool water. The pH of the solution is then adjusted to be weakly acidic, and the tubes are allowed to stand, covered at ambient temperature for sufficient amount of time for a reaction to take place, preferably between 30 minutes and 5 hours.

Samples exhibiting any color change indicate the presence of elevated levels of melanin within the urine that might interfere with immunoassay or GC/MS analysis. The precipitates can be removed from the sample by conventional filtration techniques. Alternatively, demelanization of untreated samples can be performed with any of the above-listed demelanizing agents.

Upon completion of the de-melanizing process, the melanin-free sample is subjected to well known sample preparation procedures for immunoassay or GC/MS analysis for a THC metabolite.

In a second embodiment of the present invention, a GC/MS is adjusted before or after analysis of a sample to subtract for the signal intensity due to the presence of melanin in the sample. The ion ratio pattern for a THC metabolite reference can be determined and any deviation from that pattern can be subtracted as a portion of the "noise level" due to melanin interference. Likewise the GC/MS can be pretuned to subtract this "noise level".

The following specific examples will illustrate the invention as it applies in particular to the removal or subtraction of melanin from urine specimens. It will be appreciated that other examples will be apparent to those of ordinary skill in the art and that the invention is not limited to these specific illustrative examples.

EXAMPLE 1

A human urine specimen is analyzed by GC/MS for the presence of a THC metabolite. The specimen is obtained from a black male who has undergone supervised abstinence from the use of marijuana and therefore should not exhibit the presence of THC in his urine. The results of the analysis indicate that approximately 5 ng/ml THC metabolite are present in his urine.

Extraction Procedure

A 10 ml aliquot of the human urine specimen is placed in a test tube. A 1.0 ml aliquot of 10 N potassium hydroxide is added to the urine, and then 100 ul of a deuterated 100 ng/ml THC-COOH internal standard is added. The tube is incubated in a 50°-60° C. waterbath for 15 minutes. The tube is removed from the water bath and 1.0 ml of 1.0 M phosphate buffer (pH 9.0) and 0.6 ml concentrated hydrochloric acid are added. The solution is mixed well and allowed to cool to room temperature.

The pH is adjusted to 9.0 using 10 N potassium hydroxide and concentrated hydrochloric acid as needed. The urine appears turbid at this point.

The tube is centrifuged at 2000 rpm for 2-3 minutes. The supernatant is decanted into a 50 ml plastic centrifuge tube containing the resin from a DuPont ® Type A extraction cartridge and is mixed. The tube is incubated at room temperature for 10 minutes with occasional mixing to resuspend the resin. The tube is then centrifuged for 1-2 minutes at 1000 rpm.

A DuPont ® Prep TM I Automated Sample Processor is prepared for sample processing by adding 24 ml of methanol (Spectrograde) to the solvent 1 reservoir and 24 ml of ethyl acetate:methanol:acetic acid (90:10:4) to the solvent 2 reservoir and then by dialing in Program 13. The extraction solution is prepared shortly before use.

Program 13 is a ten step extraction procedure, outlined below, having a duration of approximately ten minutes. The details of the extraction performed under Program 13 are contained in the Prep TM I Automated Sample Processor Instrument Instruction Manual which is incorporated herein by reference.

The tube is removed from the centrifuge and the supernatant aspirated leaving approximately 2.0 ml of the resin. The urine/resin mixture is resuspended and is poured into the appropriate Prep TM I cartridge. The tube is washed with approximately 2 ml of deionized water and the washings are added to the cartridge.

The Prep TM I cartridge is placed in the Prep TM I Automated Sample Processor and processed in the conventional manner according to Program 13. Generally, the extraction procedure of Program 13 includes the following steps: The sample is placed in an extraction cartridge containing a resin bed. The cartridge is placed within the rotor of the Prep TM I and is centrifuged in one direction at a low speed (approximately 50 rpm) to force the sample onto the resin. The lipophilic sample components are retained by the resin while other materials pass through the resin and collect in the effluent cup. An appropriate amount of wash solvent from solvent reservoir 1 is automatically added to the cartridge while the rotor is spinning. The wash solvent removes unsorbed sample components from the resin bed. The rotor speed is then increased to approximately 1800 rpm to remove as much of the wash solvent as possible. The direction of rotor spin is then reversed to align the cartridge with a recovery cup, and an appropriate amount of an eluting solvent from solvent reservoir 2 is automatically dispensed into the cartridge while the rotor is spinning. The eluting solvent elutes the lipophilic components from the resin bed and the components are collected in the recovery cup. The contents of the collection cup are then transferred into a 15 ml conical centrifuge tube.

The tube is placed in a sample concentrator and evaporated to dryness at 50°-60° C. The residue is dissolved in 100 ul of a 1:15 mixture of 25% aqueous tetramethylammonium hydroxide and dimethyl sulfoxide and is vortexed. After waiting 2 minutes, 5 ul of iodomethane is added and the solution mixed. Additional iodomethane, to a maximum of 15 ul, is added until cloudiness is observed.

After an additional 5 minutes, 0.2 ml of 0.1 N hydrochloric acid and 1.0 ml Iso-octane (Spectrograde) are added. Extraction is performed by vortexing the mixture for 1 minute.

The upper layer of the extraction solution is transferred into a clean test tube. Care is taken not to touch the bottom layer. The tube is placed in a 50°-60° C. heating block and evaporated to dryness using the air manifolds.

GC/MS Analysis

The specimen is injected into the splitless injector of a Hewlett-Packard gas chromatograph coupled to a mass spectrometer wherein selective ions are monitored (GC/SIM). Ions 316, 360 and 375 are monitored for the deuterated internal standard, and ions 313, 357 and 372 are monitored for the THC metabolite. These ions represent three of the major ion fragments normally associated with these molecules.

Table 1 indicates the concentration of each ion fragment found in the GC peak identified as the THC metabolite. The results indicated that the specimen contains approximately 5 ng/ml THC metabolite.

EXAMPLE 2

A full GC/MS scan is performed on the extracted urine sample obtained in Example 1 to provide a "fingerprint" of the ion fragments present in the GC peak identified as the THC metabolite. FIG. 1 shows the chromatogram and a bar chart of the relative abundance of each ion fragment present in the peak identified as the THC metabolite. The "cross-hair" mark on the chromatogram in FIG. 1 indicates the peak which was scanned. The numerical results are set forth in Table 2.

The scan indicates 19 ion fragments within the peak identified as the THC metabolite. Of course, some of these ion fragments, namely 316, 360 and 375, are attributable to the internal standard.

EXAMPLE 3

The urine specimen of Example 1 is de-melanized in accordance with the present invention and reanalyzed. The results indicate that no THC metabolite is present in the de-melanized sample and that the detection of THC metabolite in Examples 1 and 2 were false.

De-melanizing Procedure

A fresh aqueous solution of sodium nitroferricyanide solution (the de-melanizing agent) is prepared by the addition of 5.0 g sodium nitroferricyanide to 100 ml water. A 2 ml aliquot of the urine specimen of Example 1 is placed in a test tube. Three drops of the de-melanizing agent solution are added to the urine aliquot. The solution is made weakly alkaline by the dropwise addition of a solution of sodium hydroxide (1g/25ml dH$_2$O) as the contents of the test tube are mixed. The solution is then mixed thoroughly for one minute and the tube is cooled in a water bath containing cold tap water for 5 minutes. The mixture is then weakly acidified with the dropwise addition of an acetic acid solution (33 ml glacial acetic acid/100 ml H$_2$O). The mixture is allowed to stand at room temperature for two hours. A blue precipitate forms which indicates a level 2 melanin content. Level 2 melanin content indicates a significantly larger amount of melanin than is contained in normal Caucasian urine.

An aliquot of the supernatent is transferred to a fresh tube and the extraction procedure described in Example 1 is performed. The demelanized sample is analyzed by GC/MS.

GC/MS Analysis

Figure 2:
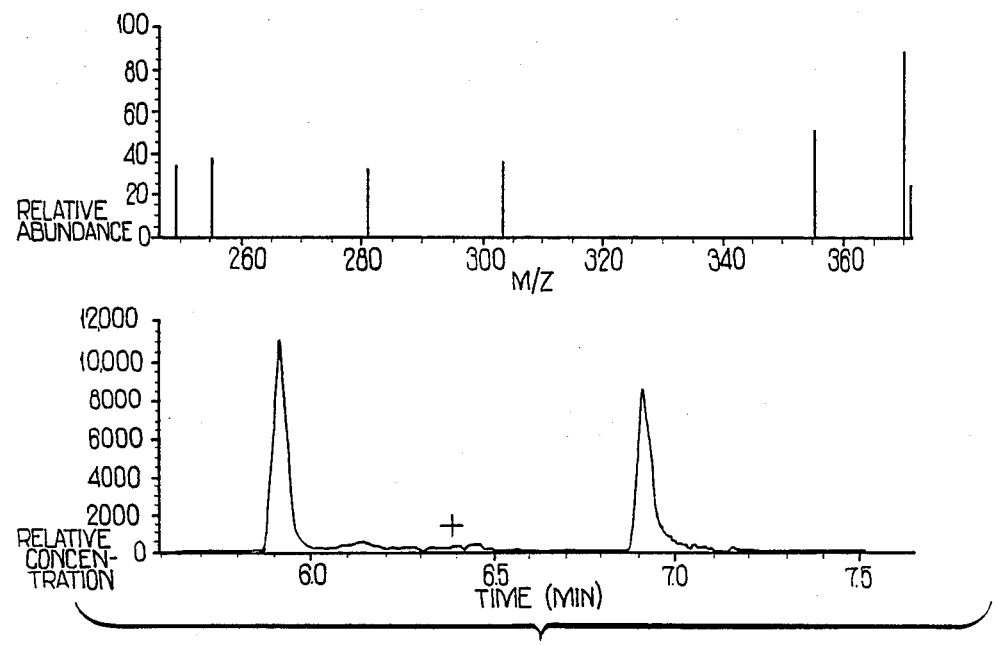
FIG. 2 is a representative chromatogram and bar charts or mass spectrum, showing the relative abundance of each ion fragment present in the peak identified as a THC metabolite after a sample is demelanized in accordance with the present invention.

Full scan analysis by GC/MS provides the data set forth in Table 3. The chromatogram and bar graph of the relative abundance of ion fragments are set forth in FIG. 2. The disappearance of the peak at the 6.4 minute retention time indicates that the specimen is successfully de-melanized by the chemical process of precipitation.

EXAMPLE 4

The de-melanized sample prepared in Example 3 is analyzed by GC/SIM under the same conditions as in Example 1. Once again, ions 313, 357 and 372 are monitored for the presence of the THC metabolite. The results set forth in Table 4 indicated that ion 372 is not present. This is misinterpreted to mean that no THC metabolite is present in the sample.

The results indicate that the substance initially identified in Example 1 as the THC metabolite is actually melanin. Both melanin and the THC metabolite molecules fragment into ions with an m/z equal to 372. Misinterpretation of the results can thus be avoided by precipitating the melanin in the urine prior to GC/MS or GC/SIM analysis in accordance with the present invention.

The following examples further show that melanin produces an m/z of 372 which may interfere in a test for a THC metabolite.

EXAMPLE 5

Urine samples are obtained from two black males who have no history of marijuana use. The specimens, identified as 6005 and 4847, are extracted and analyzed according to the procedures described in Example 1. Tables 5 and 6 set forth the results of the GC/SIM analysis for samples 6005 and 4847 respectively.

Sample 6005 shows no evidence of a THC metabolite. No ion with an m/z of 357 is found; however a small amount (0.1425 ng/ml) of the ion fragment with an m/z of 372 is detected. Sample 4847 "suggests" the presence of the THC metabolite in that all three of the monitored ions are detected with the concentration of ion 372 being 0.2592 ng/ml.

EXAMPLE 6

A black male with a history of marijuana use provides a urine specimen after three months of marijuana abstinence. The specimen is labeled 251-27-5187 and is extracted and analyzed according to the procedure described in Example 1. The results of the GC/SIM analysis is displayed in Table 7.

The three THC metabolite ions are present in the sample with concentrations ranging from 0.3903 to 1.119 ng/ml. This sample would be misinterpreted by many laboratories as being positive for THC metabolite especially in view of the fact that the specimen came from an individual who has tested positively for THC metabolite in the past.

EXAMPLE 7

A human urine specimen is de-melanized with a solution of acidified ferric chloride in water according to the following procedure. A 1 ml solution of 10g ferric chloride in 100 ml of 1.2M HCl is added to 5 ml of the urine specimen. The specimen rapidly changes from yellow to brown. The dark brown color indicates the presence of large amounts of melanin in the specimen.

EXAMPLE 8

A human urine specimen is de-melanized with hydroquinone and ferricyanide according to the following procedure. A solution containing 3 mM hydroquinone (p-dihydroxybenzene) and 6.0 mM ferricyanide is prepared. Several drops of the solution are added to 5 ml of the urine specimen. The pH of the mixture is adjusted to 7.4 with 0.1 M phosphate buffer. The mixture is kept in the dark until the amount of ferricyanide reduction is measured with a spectrometer. The amount of ferricyanide reduction is compared to a standard curve to determine the melanin level of the specimen.

EXAMPLE 9

A GC/MS instrument is adjusted to subtract the ion abundance contributed by melanin according to the following procedure. The ion ratio pattern for an authenticated THC metabolite reference on a particular day has a signal intensity of 100 for ion 313, a signal intensity of 76 for ion 357 and a signal intensity of 45 for ion 372. Therefore, a specimen is considered positive for marijuana on that particular day if it gives an ion ratio of 100:76:45 on channels 313, 357 and 372 respectively.

A non-demelanized aliquot of a specimen, which turns blue when sodium nitroferricyanide is added, is analyzed by GC/MS. The ion ratio pattern obtained for the specimen is a signal intensity of 95 for ion 357 and a signal intensity of 45 for ion 372. The signal intensity of the 357 ion for the specimen (95) is approximately 20% higher than the signal intensity of the 357 ion generated by the THC metabolite reference (76) giving an ion ratio of 0:95:45. Therefore, a 20% "noise level" is attributed to the specimen and can be subtracted from the 372 signal intensity for that particular specimen.

The above data demonstrates that there is a substance in the urine of individuals with darker skin that can be mistakenly interpreted as being THC metabolite. This substance is most likely a melanin metabolite with an ion fragment having an m/z of 372. By utilizing the preferred embodiment of the method of the present invention, a substantial quantity of melanin present in the urine sample is precipitated so that it is not mistakenly interpreted as being a THC metabolite. Utilization of the second embodiment of the method of the present invention allows for the subtraction of any signal intensity due to melanin from the GC/MS results.

Use of the method of the present invention, therefore, will eliminate a large number of the false positive test results that frequently occur in drug testing analysis.

It should be understood that the foregoing relates only to preferred embodiments of the present invention and that numerous modifications or alterations may be made therein without departing from the spirit and scope of the invention as set forth in the appended claims.

TABLE 1

GC/SIM Analysis of Human Urine Specimen Without Melanin Precipitation

| Peak Number | Time (min) | Ion | Compound | Area | Concentration |
|---|---|---|---|---|---|
| 1 + internal std | 6.816 | 316 | internal std | 19787 | 20.00 ng/ml |
| 2 | 6.817 | 360 | internal std | 14052 | 20.04 ng/ml |
| 3 | 6.817 | 375 | internal std | 9219 | 20.40 ng/ml |
| 4 | 6.835 | 313 | THC | 4822 | 4.82 ng/ml |
| 5 | 6.838 | 357 | THC | 3921 | 5.126 ng/ml |
| 6 | 6.839 | 372 | THC | 2100 | 4.784 ng/ml |

TABLE 2

Full GC/MS Scan of Human Urine Specimen Without Melanin Precipitation

| m/z | Abundance |
|---|---|
| 221.10 | 31 |
| 301.15 | 43 |
| 316.20 | 368 |
| 357.15 | 166 |
| 372.25 | 78 |
| 248.20 | 22 |
| 313.20 | 175 |
| 317.20 | 85 |
| 359.35 | 41 |
| 375.35 | 207 |
| 281.05 | 52 |
| 314.20 | 52 |
| 341.20 | 23 |
| 360.25 | 288 |
| 376.25 | 46 |
| 297.25 | 30 |
| 315.20 | 44 |
| 344.30 | 40 |
| 361.35 | 79 |

TABLE 3

Full GC/MS Scan of Human Urine Specimen After Melanin Precipitation

| m/z | Abundance |
|---|---|
| 249.20 | 35 |
| 355.25 | 50 |
| 255.30 | 37 |
| 370.35 | 90 |
| 281.05 | 33 |
| 371.35 | 26 |
| 303.35 | 36 |

TABLE 4

GC/SIM Analysis of Human Urine Specimen After Melanin Precipitation

| Peak Number | Ret. Time (min) | Ion | Compound | Area | Concentration |
|---|---|---|---|---|---|
| 1 + internal std | 6.826 | 316 | internal std | 1850 | 20.00 ng/ml |
| 2 | 6.830 | 360 | internal std | 1266 | 19.30 ng/ml |
| 3 | 6.824 | 375 | internal std | 817 | 19.34 ng/ml |
| 4 | 6.895 | 313 | THC | 839 | 8.973 ng/ml |
| 5 | 6.838 | 357 | THC | 57 | 0.7952 ng/ml |
| 6 | — | 372 | THC | not found | |

TABLE 5

GC/SIM Analysis of Sample 6005 Without Melanin Precipitation

| Peak Number | Ret. Time (min) | Ion | Compound | Area | Concentration |
|---|---|---|---|---|---|
| 1 + internal std | 6.823 | 316 | internal std | 18697 | 20.00 ng/ml |
| 2 | 6.824 | 360 | internal std | 13158 | 19.86 ng/ml |
| 3 | 6.824 | 375 | internal std | 8927 | 20.91 ng/ml |
| 4 | 6.846 | 313 | THC | 196 | 0.2078 ng/ml |
| 5 | — | 357 | THC | not found | |
| 6 | 6.849 | 372 | THC | 59 | 0.1425 ng/ml |

TABLE 6

GC/SIM Analysis of Sample 4847 Without Melanin Precipitation

| Peak Number | Ret. Time (min) | Ion | Compound | Area | Concentration |
|---|---|---|---|---|---|
| 1 + internal std | 6.831 | 316 | internal std | 17828 | 20.00 ng/ml |
| 2 | 6.834 | 360 | internal std | 13008 | 20.59 ng/ml |
| 3 | 6.834 | 375 | internal std | 8771 | 21.54 ng/ml |
| 4 | 6.854 | 313 | THC | 232 | 0.2576 ng/ml |
| 5 | 6.853 | 357 | THC | 106 | 0.1532 ng/ml |
| 6 | 6.858 | 372 | THC | 102 | 0.2592 ng/ml |

TABLE 7

GC/SIM Analysis of Sample 251-27-5187 Without Melanin Precipitation

| Peak Number | Ret. Time (min) | Ion | Compound | Area | Concentration |
|---|---|---|---|---|---|
| 1 + internal std | 6.830 | 316 | internal std | 15413 | 20.00 ng/ml |
| 2 | 6.831 | 360 | internal std | 11366 | 20.81 ng/ml |
| 3 | 6.831 | 375 | internal std | 7493 | 21.29 ng/ml |
| 4 | 6.860 | 313 | THC | 872 | 1.119 ng/ml |
| 5 | 6.853 | 357 | THC | 342 | 0.5740 ng/ml |
| 6 | 6.847 | 372 | THC | 133 | 0.3903 ng/ml |

I claim:

1. A method for the detection of tetrahydrocannabinol in a human urine specimen comprising the steps of:
   a. precipitating a quantity of the pigment melanin from said urine specimen by combining said urine specimen with a de-melanizing agent, rendering said urine specimen substantially de-melanized; and
   b. analyzing said de-melanized urine specimen for tetrahydrocannabinol.

2. The method of claim 1, wherein said de-melanizing agent of said precipitation step is selected from the group consisting of nitroferricyanide, acidified ferric chloride, hydroquinone, monobenzone, ammoniacal silver nitrate, and mono-and dihydroxybenzene derivates.

3. The method of claim 1, wherein said de-melanized urine specimen is analyzed by an immunoassay technique.

4. The method of claim 3, wherein said immunoassay technique is a radioimmunoassay.

5. The method of claim 1, wherein said de-melanized urine specimen is analyzed by GC/MS.

6. The method of claim 5, wherein said GC/MS utilizes selective ion monitoring.

7. A method for the detection of tetrahydrocannabinol in a human urine specimen containing the pigment melanin, comprising the steps of:
   a. adding a predetermined amount of a de-melanizing agent to said urine specimen, said amount being sufficient to react with said melanin;
   b. reacting said melanin in said urine specimen with said de-melanizing agent for a sufficient length of time so that a substantial quantity of said melanin is precipitated;
   c. separating said precipitated melanin from said urine specimen so that said urine specimen is effectively de-melanized; and
   d. analyzing said de-melanized urine specimen for the presence of tetrahydrocannabinol by conventional analytical methods.

8. The method of claim 7, wherein said de-melanizing agent is selected from the group consisting of nitroferricyanide, acidified ferric chloride, hydroquinone, monobenzone, ammoniacal silver nitrate, and mono- and dihydroxybenzene derivates.

9. The method of claim 7, wherein said de-melanized urine is analyzed by immunoassay.

10. The method of claim 7, wherein said de-melanized urine is analyzed by GC/MS.

11. A method for the detection of tetrahydrocannabinol in a human urine specimen comprising the steps of:
    a. treating said human urine specimen with a quantity of a de-melanizing agent sufficient to react with any melanin present in said human urine specimen; and
    b. analyzing said treated human urine specimen for the presence of tetrahydrocannabinol.

12. The method of claim 11, wherein said de-melanizing agent is selected from the group consisting of nitroferricyanide, acidified ferric chloride, hydroquinone, monobenzone, ammoniacal silver nitrate, and mono- and dihydroxybenzene derivates.

13. The method of claim 11 further comprising the step of removing from said human urine specimen any melanin precipitated by said de-melanizing agent prior to analyzing said human urine specimen.

14. The method of claim 11, wherein said treated human urine is analyzed by GC/MS.

15. The method of claim 14, further comprising the step of adjusting said GC/MS to subtract any signal intensity due to melanin.

16. A method for the detection of tetrahydrocannabinol in human urine specimens comprising the steps of:
    a. determining a signal intensity ion ratio pattern for a tetrahydrocannabinol reference by GC/MS;
    b. screening said human urine specimens for the presence of melanin, wherein said screening is performed by adding to each of said urine specimens a quantity of de-melanizing agent sufficient to react with any melanin present in said human urine specimens so that said human urine specimens containing melanin undergo a color change;
    c. determining a signal intensity ion ratio pattern for said melanin-containing urine specimens by GC/MS;
    d. determining any difference between said signal intensity ion ratio pattern for said reference and said signal intensity ion ratio pattern for each of said specimens containing melanin, said difference representing a noise level due to the presence of melanin; and
    e. subtracting said noise level for each of said urine specimens from said signal intensity ion ratio pattern determined for each urine specimen.

* * * * *